(12) United States Patent
Bernini Freddi et al.

(10) Patent No.: US 11,472,972 B2
(45) Date of Patent: Oct. 18, 2022

(54) 3-KETOCOUMARINS, A PROCESS FOR THEIR PREPARATION AND THEIR USE AS PHOTOINITIATORS IN PHOTOPOLYMERIZATION REACTIONS

(71) Applicant: IGM Group BV, RM Waalwijk (NL)

(72) Inventors: Andrea Bernini Freddi, Gavirate VA (IT); Marika Morone, Lipomo CO (IT); Gabriele Pietro Norcini, Comabbio VA (IT)

(73) Assignee: IGM Group BV, RM Waalwijk (NL)

( * ) Notice: Subject to any disclaimer, the term of this patent is extended or adjusted under 35 U.S.C. 154(b) by 939 days.

(21) Appl. No.: 16/310,123

(22) PCT Filed: Jun. 12, 2017

(86) PCT No.: PCT/IB2017/053456
§ 371 (c)(1),
(2) Date: Dec. 14, 2018

(87) PCT Pub. No.: WO2017/216699
PCT Pub. Date: Dec. 21, 2017

(65) Prior Publication Data
US 2019/0256723 A1 Aug. 22, 2019

(30) Foreign Application Priority Data
Jun. 17, 2016 (IT) .......................... UA2016A004470

(51) Int. Cl.
| C09D 11/101 | (2014.01) |
| C09B 57/02 | (2006.01) |
| C09D 11/30 | (2014.01) |
| C09D 143/04 | (2006.01) |
| C07D 311/16 | (2006.01) |
| C08F 2/50 | (2006.01) |

(52) U.S. Cl.
CPC .......... *C09D 11/101* (2013.01); *C07D 311/16* (2013.01); *C08F 2/50* (2013.01); *C09B 57/02* (2013.01); *C09D 11/30* (2013.01); *C09D 143/04* (2013.01)

(58) Field of Classification Search
CPC .................................................... C09D 11/101
USPC ........................................................ 549/275
See application file for complete search history.

(56) References Cited

U.S. PATENT DOCUMENTS 427,875 A 5/1890 Jones
2005/0270441 A1 12/2005 Chari et al.

FOREIGN PATENT DOCUMENTS

GB 2 189 496 10/1987
WO 2014/063997 5/2014

OTHER PUBLICATIONS

International serach report and written opinion issued from the EPO for PCT/IB2017/053456 dated Aug. 10, 2017.
Search report issued from the EPO for Italian priority application No. IT US20164470 dated Nov. 15, 2016.
International preliminary report on patentability issued from the EPO for PCT/IB2017/053456 dated Dec. 27, 2018.

*Primary Examiner* — Nizal S Chandrakumar
(74) *Attorney, Agent, or Firm* — Silvia Salvadori

(57) ABSTRACT

Subject-matter of the present invention are novel 3-ketocoumarins, a process for their preparation and their use as photoinitiators in photopolymerization reactions, advantageously in photopolymerization reactions for inkjet printing inks. The invention also concerns a process for the photopolymerization of compositions also comprising said 3-ketocoumarins.

4 Claims, No Drawings

3-KETOCOUMARINS, A PROCESS FOR THEIR PREPARATION AND THEIR USE AS PHOTOINITIATORS IN PHOTOPOLYMERIZATION REACTIONS

This application is a U.S. national stage of PCT/IB2017/053456 filed on 12 Jun. 2017, which claims priority to and the benefit of Italian Application No. UA2016A004470 filed on 17 Jun. 2016, the contents of which are incorporated herein by reference in their entireties.

SUMMARY OF THE INVENTION

Subject-matter of the present invention are novel 3-ketocoumarins, a process for their preparation and their use as photoinitiators in photopolymerization reactions, advantageously in photopolymerization reactions for inkjet printing inks. The invention also concerns a process for the photopolymerization of compositions comprising said 3-ketocoumarins.

TECHNICAL FIELD

The photopolymerizable systems contain photoinitiators that have a functional group in the molecule that, by exposing to light with suitable wavelength, generates radicals able to initiate the polymerization.

Among light radiations sources used in this field the light-emitting diodes (LED), or else a semiconductor light source, have been subject to significant development over the past few years because of their low operating temperature and very long average life when compared to that of the medium pressure mercury lamps normally used in the photopolymerization. The LED lamps are also advantageous for the intrinsically reduced dimensions of the LED units and their ability to be easily engineered, for example in commercial printing systems. When LED lamps for photopolymerizing inks and coatings are used, it is necessary to use selected photoinitiators systems that are active in wavelengths of the light coming from this source. Typically, while the mercury vapor lamps have polychrome emission spectrum covering all regions of the UV-visible spectrum from 200 to 450 nm, usually LED lamps have only a single emission band in the range 365-420 nm.

Photoinitiators are therefore needed that, by absorbing in the region between 365 and 420 nm, allow the recent development of high power LEDs to be fully exploited. Furthermore, since for LED applications high concentrations of photo-active substance are normally needed, photoinitiators should have high compatibility with the photopolymerizable system.

Thioxantones, such as isopropyl thioxantone (ITX) and derivatives thereof, and acyl phosphine oxides are photoinitiators absorbing light in this spectrum region and are commonly used in the field. Unfortunately, thioxantone derivatives commonly used both as photoinitiators and sensitizers, are subject to yellowing upon exposing to light and generate degradation products with poor stability. As a result, the initial yellowing can unpredictably change over time. This behavior unstable to the yellowing makes very difficult, especially in printing images, for example in the inkjet printing, to control the tone of color in the final images. On the other hand, acyl phosphine oxides give aldehydes with medium volatility as degradation products, thus producing an unacceptable background smell in coatings or printed images. Furthermore, the use of high quantities of acyl phosphine oxides gives safety and health issues for workers. Alpha-diketons, such as camphorquinone and derivatives thereof and 1-phenyl propanedione, are other examples of suitable photoinitiators and have been widely used in combination with LED light sources, particularly for dental applications, but unfortunately their activity is rather low, particularly in pigmented systems.

Coumarin derivatives have been used for a long time as photoinitiators and also as sensitizers, reacting at wavelengths up to about 550 nm, but always using wide spectrum actinic lamps as light sources.

GB 1,578,662 describes a composition comprising an unsaturated compound sensitive to radiations or an azide-based photopolymerizable material and, as a sensitizer, a 3-substituted coumarin, among which also the 3-ketocoumarins.

U.S. Pat. No. 4,278,751 describes a photopolymerizable composition which comprises at least one polymerizable compound containing unsaturated ethylene groups, a photopolymerization activator (photoinitiator) and a ketocoumarin substituted with an amino group as sensitizer. The usable light sources include, filtrated or not filtrated wide spectrum light sources including xenon or carbon arc lamps, and sources with narrow spectrum such as mercury vapor lamps.

U.S. Pat. No. 4,289,844 describes a photopolymerizable composition which comprises at least one polymerizable compound containing an unsaturated ethylene group, a photopolymerization activator (photoinitiator) and a sensitizer selected from 3-ketocoumarins containing alkyl or $C_1$-$C_{12}$ alkenyl groups or cyclic or heterocyclic groups having 5 to 20 carbon atoms and heteroatoms. In this patent, as a light source a medium pressure mercury lamp is used.

WO2014/063997 describes some aromatic derivatives of 3-ketocoumarins useful as photoinitiators following the exposure to LED light sources emitting at wavelengths between 365 and 420 nm. Said 3-ketocoumarins do not provoke undesired yellowings and at the same time maintain high compatibility with photopolymerizable systems. In the document 3-ketocoumarins are described that show (a) a wide series of possible substitutions on the coumarin ring ("hydrogen, halogen, $C_1$-$C_{12}$ alkyl, $C_3$-$C_{12}$ alkenyl, $C_5$-$C_6$ cycloalkyl, substituted or not substituted aryl or heteroaryl, $C_1$-$C_{12}$ alkoxy, $C_1$-$C_4$ hydroxyalkoxy, phenoxy, —COOH, —COO ($C_1$-$C_4$ alkyl), —S—$R_7$, —SO—$R_7$ or —$SO_2R_7$, wherein $R_7$ is hydrogen, $C_1$-$C_{12}$ alkyl, $C_3$-$C_{12}$ alkenyl, phenyl, substituted or not substituted aryl or heteroaryl, $C_5$-$C_6$ cycloalkyl, $C_1$-$C_{12}$ alkyl substituted by SH, —N($C_1$-$C_6$ alkyl)$_2$, pyperidinium, morpholinium, pyperazinium, —OH, —O($C_1$-$C_{12}$ alkyl), —COOH") and (b) a $C_2$-$C_{12}$ aliphatic chain on the phenyl group. Regarding the latter substitution, on the other hand in the examples only 3-ketocoumarins are depicted wherein the aliphatic chain arrives up to $C_4$ (t-Bu). Also said 3-ketocoumarins, even if effective, can however show some drawbacks, as it will be discussed herein below in the present description.

Therefore there is a growing need of developing alternative photoinitiators giving solutions to all the drawbacks of the prior art, i.e. showing an absorption in the region between 365 and 420 nm, not determining yellowing, having good photochemical reactivity, not generating smelling degradation products and that are safe for the health and environment.

OBJECTS OF THE INVENTION

It is an object of the present invention to provide novel specific derivatives of 3-ketocoumarins to be used as photoinitiators, that are not showing the problems of the photoinitiators of the prior art.

It is another object of the present invention to provide a process for the preparation of said derivatives of 3-ketocoumarins.

It is further object of the present invention to provide photopolymerizable compositions comprising said derivatives of 3-ketocoumarins and a photopolymerization process involving the use of said derivatives.

These and other objects will be set forth in the following description.

DESCRIPTION OF THE INVENTION

Subject-matter of the present invention are derivatives of 3-ketocoumarin of Formula (I):

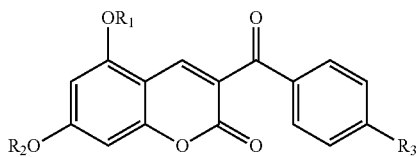

(I)

wherein:
$R_1$ and $R_2$ are, each independently, a $C_1$-$C_4$ alkyl group;
$R_3$ is selected from
- a branched $C_6$-$C_{20}$ alkyl group or a mixture of linear and branched $C_6$-$C_{20}$ alkyl groups;
- a $C_6$-$C_{20}$ alkyl-aryl, an aryl-$C_6$-$C_{20}$ alkyl, a $C_6$-$C_{20}$ alkyl-heteroaryl, a heteroaryl-$C_6$-$C_{20}$ alkyl, a $C_6$-$C_{20}$ alkylene oxide, a —COO— $C_6$-$C_{20}$ alkyl, and COOaryl.

The term "alkyl" means, according to the present invention, a saturated linear or branched alkyl group.

The $C_1$-$C_4$ alkyl group includes methyl, ethyl, n-propyl, i-propyl, n-butyl, i-butyl, t-butyl group, the methyl group being the preferred one.

According to a preferred embodiment, $R_1$ and $R_2$ are the same $C_1$-$C_4$ alkyl, advantageously methyl.

The $C_6$-$C_{14}$ alkyl group includes all the alkyls having 6 to 14 carbon atoms, in all the possible isomers thereof.

According to a preferred embodiment, $C_6$-$C_{14}$ alkyl is advantageously $C_9$-$C_{14}$ alkyl.

According to the present invention, the expression "mixture of $C_6$-$C_{14}$ alkyl groups" or "$C_9$-$C_{14}$ alkyl" means that $R_3$ cannot be a single alkyl, but can be constituted by a mixture of different alkyls having the same length or different length and/or which comprises different alkyl isomers. Said mixture can comprise linear and branched alkyls.

According to a preferred embodiment, the mixture of $C_6$-$C_{14}$ alkyl groups is advantageously a mixture of $C_9$-$C_{14}$ alkyl groups, more preferably a mixture of alkyl $C_{10}$-$C_{13}$ groups as defined above.

By "$C_{10}$-$C_{13}$ alkyl mixture" is herein meant a mixture of alkyl groups essentially composed of $C_{10}$-$C_{13}$ alkyls generally comprising up to 2%, preferably up to 1% by weight of alkyls which are $C_9$ and $C_{14}$ long.

According to a more preferred embodiment, the mixture of $C_6$-$C_{14}$ alkyl groups is constituted by alkyl $C_{10}$-$C_{13}$ linear groups such as those described herein above, in admixture with their branched isomers.

According to a more preferred embodiment, the mixture of $C_6$-$C_{14}$ alkyl groups is constituted from more than 50%, for example more than 60%, advantageously more than 75%, by alkyl $C_{10}$-$C_{13}$ linear groups such as those described herein above, i.e. containing traces of alkyls which are $C_9$ and $C_{14}$ long, and for the remaining percentage by their branched isomers.

For example, advantageously, the mixture of $C_6$-$C_{14}$ alkyl groups is constituted from 50 to 99%, preferably from 60 to 90%, even more preferably from 75 to 87%, for example from 78 to 85%, by alkyl $C_{10}$-$C_{13}$ linear groups such as those described above, and for the remaining percentage by their branched isomers.

According to a more preferred embodiment, $R_1$ and $R_2$ are both methyl and $R_3$ is a mixture constituted from 78% to 85% by alkyl $C_{10}$-$C_{13}$ linear groups such as those described above and for the remaining percentage by their branched isomers.

According to an embodiment, when $R_3$ is a mixture of $C_6$-$C_{20}$ alkyl linear and branched groups, then one between $R_1$ and $R_2$ is not a linear propyl group.

In the description, "aryl" means an aromatic hydrocarbon group having 6 to 10 carbon atoms, possibly substituted, and examples include, for example, the phenyl group, the naphthyl group, the azulenyl group, and the likes.

In the description, "heteroaryl means a monocycle, polycycle or a condensed ring of the heterocyclic aromatic type from 5 to 10 members, possibly substituted, containing 1 to 4 heteroatoms selected from oxygen atom, sulphur atom and nitrogen atom as constituents of the ring. Examples include, for example, the furyl group, the thienyl group, the pyrrolyl group, the oxazolyl group, the isoxazolyl group, the thiazolyl group, the isothiazolyl group, the imidazolyl group, the pyrazolyl group, the oxadiazolyl group, the thiadiazolyl group, the triazolyl group, the tetrazolyl group, the pyridyl group, the pyrimidyl group, the pyrazinyl group, the pyridazinyl group, the benzofuranyl group, the isobenzofuranyl group, the benzothienyl group, the indolyl group, the isoindolyl group, the indazolyl group, the benzimidazolyl group, the benzoxazolyl group, the benzisoxazolyl group, the benzothiazolyl group, the benzoisothiazolyl group, the benzoxadiazolyl group, the benzothiadiazolyl group, the benzotriazolyl group, the quinolinyl group, the isoquinolinyl group, the cinnolyl group, the quinazolyl group, the quinoxalynyl group, the phthalazinyl group, the naphthyridinyl group, the purinyl group, the pteridinyl group, the furopyridyl group, the thienopyridyl group, the pyrrolopyridyl group, the oxazolpyridyl group, the thiazopyridyl group, the imidazopyridyl group, and the like.

The compounds of Formula (I) can be obtained according to the conventional techniques known to the expert in the art. For example, they can be synthesized by the Knoevenagel reaction, providing for the condensation of 2-hydroxy-1-arylaldehyde (-arylketone) with the corresponding alkylbenzoylacetate, depicted in the following scheme:

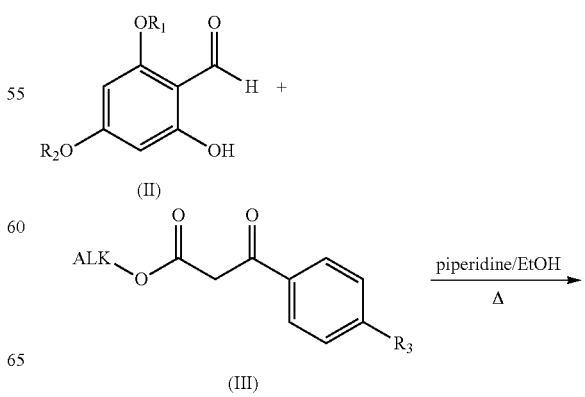

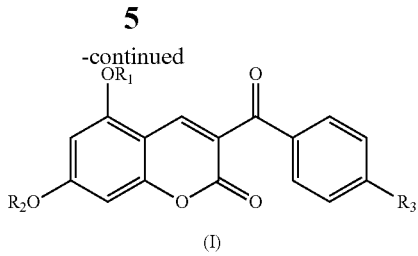

wherein ALK is an alkyl group, for example methyl, and $R_1$, $R_2$ and $R_3$ are as described above.

The compounds of formula (II) and (III) can be prepared according to known processes.

For the preparation of a preferred compound according to the invention, wherein $R_3$ is a mixture of $C_9$-$C_{14}$ alkyl groups, the compound of Formula (III) is prepared by a mixture of linear and branched $C_{10}$-$C_{13}$ alkyl benzenes (containing $C_9$ and $C_{14}$ alkyls as traces).

Details related to the synthesis of representative compounds of the invention are reported in the Experimental Section of the present description.

The process for the preparation of the compounds of Formula (I) described above is a further subject-matter of the invention. However, other synthesis paths can be used.

The compounds of Formula (I) are useful as photoinitiators. The use of the compounds of Formula (I) as photoinitiators in photopolymerization processes is a further aspect of the present invention, as well as a method for the photopolymerization which comprises using the compounds of Formula (I) as photoinitiators.

As mentioned, by "photoinitiator" is meant a molecule having a functional group able to generate radicals (by itself or in combination with a co-initiator), which are able to initiate a polymerization by exposure to light with suitable wavelength.

The compounds of Formula (I) can be used, particularly, in photopolymerizable compositions adapted for the inclusion in inks or coatings that can be polymerized by exposure to the radiations of a LED light source.

For their use, the compounds of Formula (I) are included in photopolymerizable compositions which comprise at least one ethylenically unsaturated compound and at least one compound of Formula (I).

By "ethylenically unsaturated compound" is meant a monomer, an oligomer, a prepolymer, with at least one unsaturation, or mixtures thereof, able to participate in a radical polymerization. Combinations of monomers, oligomers and prepolymers with different degrees of unsaturation can also be used.

The monomers suitable for implementing the present invention are those commonly used in the technical field, and for example can be selected from vinyl ethers, N-vinyl pyrrolidone, N-vinyl caprolactam, mono- and poly-functional allyl ethers such as trimethylolpropane diallyl ether, styrenes and alpha methyl styrenes, (meth)acrylic acid esters with aliphatic alcohols, glycols, polyoxydryl compounds such as pentaerythrite or trimethylolpropane; vinyl alcohol esters with aliphatic or acrylic acids; maleic acid and fumaric acid derivatives.

Oligomers or prepolymers suitable for the present invention comprise, for example, polyesters, polyacrylates, polyurethanes, epoxy resins, polyethers with acrylic, maleic or fumaric functionalities.

Monomers and oligomers or prepolymers that are commonly used in photopolymerizable inks are preferred. Such compounds are known to the expert in the art and are described for example in the above mentioned Document WO2014/063997.

The photopolymerizable compositions of the invention preferably comprise 50 to 99.9% by weight of at least one ethylenically unsaturated compound and 0.1 to 35% by weight of at least one compound of Formula (I).

More preferably, photopolymerizable compositions of the invention comprise 70 to 98.9% by weight of at least one ethylenically unsaturated compound and 0.1 to 20% by weight of at least one compound of Formula (I), more preferably 0.2 to 15% by weight.

Unless otherwise stated, by the expression "by weight" is meant that the depicted percentages are by weight to the total weight of the composition.

The photopolymerizable compositions of the invention can also contain other components normally used in the field and known to the expert in the art, for example, heat stabilizers, stabilizers against the photo-oxidation, anti-oxidant agents, loads, dispersants, dyes and/or opacifying substances and other additives of general use. Other components of the photopolymerizable compositions of the invention can be non-photopolymerizable polymers that are present as chemically inert substances, for example nitro-celluloses, polyacrylic esters, polyolefins, and other compounds conventionally used in this type of compositions.

Other components of the photopolymerizable compositions of the invention can be non-photopolymerizable polymers that are present as inert substances, for example nitrocellulose, polyacrylic esters, polyolefins, etc.

The photopolymerizable compositions of the invention can also conveniently comprise a co-initiator that is a molecule acting as hydrogen donor and increasing the polymerization speed. The co-initiators are known in the art and typically are alcohols, thiols, amines or ethers having available one hydrogen bonded to one carbon adjacent to the heteroatom. Such co-initiators are generally present in quantities between 0.2 and 15% by weight, preferably between 0.2 and 8% by weight. Suitable co-initiators include, but are not limited to, aliphatic, cycloaliphatic, aromatic, aryl-aliphatic, heterocyclic, oligomeric or polymeric amines. They can be primary, secondary or tertiary amines, for example butyl amine, dibutyl amine, tributyl amine, cyclohexyl amine, benzyldimethyl amine, di-cyclohexyl amine, N-phenyl glycine, triethyl amine, phenyldiethanol amine, triethanol amine, piperidine, piperazine, morpholine, pyridine, quinoline, dimethylamino benzoic acid esters, Michler ketone (4,4'-bis-dimethyl aminobenzophenone) and its derivatives.

As co-initiators based on amines, acrylates containing an amine can also be used; examples of such acrylates include the acrylates modified by reaction with a primary or secondary amine, which are described in U.S. Pat. No. 3,844,916, EP 280222, U.S. Pat. Nos. 5,482,649, 5,734,002 and US2013/0012611.

Preferred co-initiators are Esacure A198 (bis-N,N-[4-dimethylaminobenzoyl) oxyethylen-1-yl]-methylamine), Esacure EDB (ethyl-4-dimethylamino benzoate) and Photomer 4250, all sold by IGM Resins B.V., 2-ethylhexyl-4-dimethylaminobenzoate and N-phenyl glycine.

The photopolymerizable compositions of the invention can also conveniently comprise other photoinitiators commonly used in the field.

Other possible photoinitiators, the co-initiators and further possible components that can be comprised in the composition of the invention are described for example in the above mentioned document WO2014/063997.

According to one of its preferred aspects, the compounds of Formula (I) can be used as sensitizing agents of photoinitiators that can be sensitized in photopolymerizable compositions.

By "sensitizer" or "sensitizing agent" is meant a molecule that, through a energy transfer process, activates a photoinitiator at a wavelength at which the photoinitiator alone would not be reactive.

The photopolymerizable compositions comprising one or more compounds of Formula (I) as sensitizing agents, can comprise 70 to 98.9% by weight of at least one ethylenically unsaturated compound, 0.1 to 10% by weight of at least one compound of Formula (I) and 1 to 15% by weight of at least one photoinitiator that can be sensitized, for example a ketosulfone or an alpha-aminoketone and, possibly, 0.2 to 8% by weight of a co-initiator.

In the above compositions, the preferred photoinitiators that can be sensitized are 1-[4-[(4-benzoyl-phenyl)-thio]-phenyl]-2-methyl, 2-[(4-methyl-phenyl)-sulfonyl]-propan-1-one (Esacure 1001, sold by IGM Resins B.V.), 2-methyl-1-(4-methylthiophenyl)-2-morpholinopropan-1-one), 2-benzyl-2-dimethylamino-1-(4-morpholino phenyl)-butan-1-one, and 2-(dimethylamino)-2[(4-methylphenyl)methyl]-1-[4-(4-morpholinyl)phenyl]-1-butanone.

The compounds of Formula (I) can be included both in transparent photopolymerizable compositions and in non-transparent or colored compositions and, particularly, are useful for the preparation of inks that are photopolymerizable by a LED light source.

The photoinitiators and compositions of the invention are particularly suitable for the preparation of photopolymerizable inks for inkjet printing.

For this reason, in addition, the photopolymerizable compositions of the invention can comprise coloring compounds to an extent of 0.01-30% by weight.

The coloring compounds that can be used in the inks photopolymerizable by the LED light of the invention can be dyes, pigments or a combination thereof.

Organic and/or inorganic pigments can be used. The coloring compounds are preferably polymeric pigments or dyes, more preferably pigments. The pigments can be black, white, cyan, magenta, yellow, red, orange, violet, blue, green, brown, or mixtures thereof, as well as other conventional and well known to the expert in the art pigments.

Examples of organic pigments are insoluble azoic pigments, azo-condensed pigments, azo-lakes, and azo-chelated pigments, polycyclic pigments, such as the pigments based on phthalocyanines, pigments based on perylene and perinone, anthraquinone pigments, quinacridone pigments, dioxane pigments, thioindigo pigments, isoindolinone pigments and pigments based on quinophthalone; chelated dyes, such as basic chelated dyes and acidic chelated dyes; coloring lakes, such as for example basic coloring lakes and acidic coloring lakes; nitro pigments, nitroso pigments, aniline black and fluorescent pigments.

In the white inks photopolymerizable via LED, the white coloring compounds are preferably present from 3 to 30% by weight of the ink composition and more preferably 5 to 25%. Generally, other dyes are present to an extent of 0.01-10% by weight, preferably between 0.1 and 5% by weight, in the LED-photopolymerizable inks of the invention.

The coloring compounds for inkjet printing are particularly preferred.

In addition to the main components described above, the photopolymerizable compositions and inks of the invention can also contain other specific components, such as co-initiators and other photoinitiators, such as those described in the previous paragraphs and, in the same quantities, can also contain dispersants, surfactants and other additives conventionally used and well known to the expert in the art. Such components are, for example, described in the document WO2014/063997.

The compositions and inks described above are further subject-matters of the present invention.

According to another of its aspects, subject-matter of the invention is a process for photopolymerizing compositions and photopolymerizable inks, which comprises the following steps:

I) preparing a photopolymerizable composition comprising:
   a. 50 to 99.9% by weight, preferably 70 to 98.9% by weight, of at least one ethylenically unsaturated compound;
   b. 0.1 to 35% by weight, preferably 0.1 to 20% by weight and more preferably 0.2 to 15% by weight, of at least one compound of Formula (I), wherein $R_1$, $R_2$ and $R_3$ are as defined above; and II) photopolymerizing the composition of step (I) with a LED light source which emits light with wavelengths between 365 nm and 420 nm, preferably between 365 nm and 395 nm.

According to a preferred embodiment, in the process for the photopolymerization of the invention, the compound of Formula (I) is as defined in the preferred embodiments described above.

Possibly, said photopolymerizable composition can be applied to a substrate prior to carry out the step of photopolymerization with said LED light source. Examples of substrates include, but are not limited to, polyethylene, polypropylene, terephthalate polyester, nylon, paper, cardboard, wood, metal, glass, and other substrates well known to the expert in the art.

Examples of application processes include, but are not limited to, the flexographic printing, etching, serigraphy, inkjet printing, lithography or gravure, spray coating, airless spray, cylinder printing, flexography, etching, curtain coater, slot (four-color printing), brush and wire-wound roller. However, other methods for applying said photopolymerizable composition will be apparent to the expert in the art.

Said photopolymerizable composition can be applied to a substrate that already comprises a coated or printed layer. After photopolymerization with a LED light source, said photopolymerizable composition can be over-printed or coated with one or more compositions suitable for printing or coating.

It is a further aspect of the invention the article obtained upon application of said photopolymerizable composition on said substrate by said coating o printing means, and by photopolymerizing through said LED light source, with or without further article processing, through a further coating or printing.

Surprisingly, it has been found that the compounds of Formula (I) obviate the drawbacks of the prior art, as they show an absorption in the region between 365 and 420 nm (and therefore can be used as photoinitiators by LED lamps), they do not determine yellowing, have good photochemical reactivity, do not generate smelling degradation products and are safe for the health and environment.

Surprisingly, it has been found that the compounds of Formula (I) show higher reactivity during the photopolymerization process and determine lower yellowing compared to the compounds described in WO2014/063997.

Furthermore, in a completely unexpected way, the compounds of Formula (I) showed higher reactivity in the polymerization process, as demonstrated by Example 6.3. In said example, equivalent quantities by weight of two products have been reacted: a compound of Formula (I) and a comparative compound (the compound expressly described in Example 10 of WO2014/063997). The tested compound of Formula (I) has molecular weight higher than the comparative compound and therefore is evident that, in the test, the moles of said compound of Formula (I) that are present in the reaction mixture are less than the moles of the comparative compound (in the specific case, lower by about 30%). Quite surprisingly, the conversion of the double bonds in the polymerization reaction was equivalent. Therefore, it has been demonstrated the higher reactivity per mole of the tested compound of Formula (I) with respect to the comparative compound.

In addition to this, in a completely unexpected way, the compounds of Formula (I) showed higher reactivity also with respect to the compounds of Formula (I) wherein $R_3$ represents an alkyl of the same length but linear, as demonstrated in the comparative examples reported in the Experimental Section.

EXPERIMENTAL SECTION

Example 1

Preparation of 3-(4-(2-ethylhexyl)benzoyl)-5,7-dimethoxycoumarin

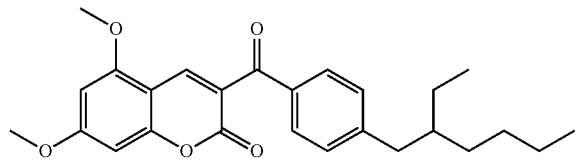 [SMILES: CCCCC(CC)Cc1ccc(C(=O)c2cc3c(OC)cc(OC)cc3oc2=O)cc1]

Example 1.1

Preparation of 1-(4-(2-ethylhexyl)phenyl)ethan-1-one

To a solution of 4.65 g (24.47 mmoles) of (2-ethylhexyl)benzene and 2.02 g of acetyl chloride (25.69 mmol) in 20 ml of dichloromethane, 3.42 g (25.69 mmol) aluminum chloride has been added, in about 30 seconds and by maintaining the temperature between 0° and 5° C. After 3 hours at ambient temperature, the reaction mixture was poured in a mixture of 50 ml water and ice containing 1 ml 37% HCl. The organic phase has been separated and washed with 3×50 ml water, dried on sodium sulfate, filtered and the solvent has been removed by vacuum distillation. The product has been purified by flash chromatography on silica gel, by eluting with toluene. Thus, 1.1 g (yield 19%) title compound as yellow oil has been obtained.
$^1$H-NMR (CDCl3, δ ppm): 0.88 (t, 6H), 1.20-1.32 (m, 8H), 1.57-1.62 (m, 1H), 2.39 (s, 1H), 2.58-2.60 (m, 4H), 7.24 (d, 2H), 7.88 (d, 2H)

Example 1.2

Preparation of methyl 3-(4-(2-ethylhexyl)phenyl)-3-oxopropanoate

To a flask, NaH (0.43 g, 60% w/w, 10.84 mmoles), dimethyl carbonate (0.70 g, 7.75 mmoles) and toluene (15 ml) have been loaded under nitrogen purging. The mixture is heated to reflux then is added dropwise to a solution of 1-(4-(2-ethylhexyl)phenyl)ethan-1-one (3.87 mmoles) in toluene (5 ml) in 0.5 hours. The mixture is allowed to react under reflux until the TLC (thin layer chromatography) shows the ketone has totally disappeared. After cooling, the reaction mixture is quenched with iced and acidified water with 3 M HCl up to pH 2-3. The organic phase has been separated and washed with 3×50 ml water, dried on sodium sulfate, filtered and the solvent has been removed by vacuum distillation. Thus, 0.90 g title compound has been obtained as oil that has been used as such in the following reaction.

Example 1.3

Preparation of 3-(4-(2-ethylhexyl)benzoyl)-5,7-dimethoxycoumarin

To a solution of 0.5 g (2.75 mmoles) 4,6-dimethoxy-2-hydroxy-benzaldehyde and 0.8 g (2.75 mmoles) methyl 3-(4-(2-ethylhexyl)phenyl)-3-oxopropanoate in 15 ml ethanol, 0.5 ml piperidine has been added. After 3 hours under reflux, the reaction mixture has been cooled, washed with an acidic aqueous solution and extracted with dichloromethane. The organic phase has been separated and washed with 3×30 ml water, dried on sodium sulfate, filtered and the solvent has been removed by vacuum distillation. The product has been purified by flash chromatography on silica gel, by eluting with a gradient from $CH_2Cl_2$ to 9:1 $CH_2Cl_2$/AcOEt. Thus, 0.6 g (yield 52%) title compound has been obtained as yellow oil that has then solidified.
$^1$H-NMR (CDCl3, δ ppm): 0.88 (t, 6H), 1.20-1.32 (m, 8H), 1.57-1.62 (m, 1H), 2.59 (d, 2H), 3.90 (s, 6H), 6.3 (d, 1H), 6.47 (d, 1H), 7.22 (d, 2H), 7.78 (d, 2H), 8.40 (s, 1H)

Example 2

Preparation of 3-(4-isomeric mixture $C_{10}$-$C_{13}$ benzoyl)-5,7-dimethoxycoumarin

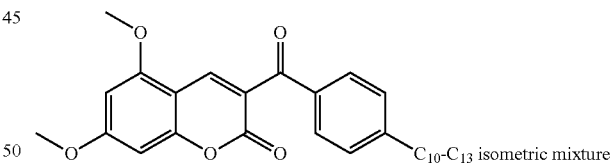

Example 2.1

Preparation of methyl-3-(4-isomeric mixture $C_{10}$-$C_{13}$ phenyl)-3-oxopropanoate By operating as described in Example 1.1 and 1.2, but using as a starting product a mixture of linear and branched $C_{10}$-$C_{13}$ alkyl benzenes (containing $C_9$ and $C_{14}$ alkyls as traces, about 1% by weight in total) currently sold with the brand name ISORCHEM® 113 (Sasol, Italy), the title compound is obtained. The title compound has been used directly in the following reaction without any further purification.

Example 2.2

Preparation of 3-(4-isomeric mixture $C_{10}$-$C_{13}$ benzoyl)-5,7-dimethoxycoumarin To a solution of 5 g (27.4 mmoles) 4,6-dimethoxy-2-hydroxy-benzaldehyde and 9.50 g (27.4 mmoles) methyl-3-(4-isomeric mixture $C_{10}H_{21}$-$C_{13}H_{27}$phenyl)-3-oxopropanoate in 20 ml ethanol, 2.33 g piperidine has been added. After 3 hours under reflux, the reaction mixture has been cooled, washed with acidified water and extracted with AcOEt. The organic solvent has been eliminated by vacuum distillation. The crude compound has been used by flash chromatography by eluting with a 95/5 toluene/AcOEt mixture. Yellow oil has been obtained, that has been crystallized from ethanol thus giving 5.7 g pale yellow solid (yield 43%).

m.p. 68-69° C.

$^1$H-NMR (CDCl3, δ ppm): 0.81-0.89 (m, 3H), 1.05-1.65 (m, 21H), 2.32-2.62 (m, 1H), 3.90 (s, 6H), 6.31 (d, 1H), 6.46 (d, 1H), 7.22-7.28 (m, 2H), 7.78 (d, 2H), 8.39-8.41 (m, 1H).

Example 3

Preparation of 5,7-dimethoxy-3-(4-(3,5,5-trimethylhexyl)benzoyl) coumarin

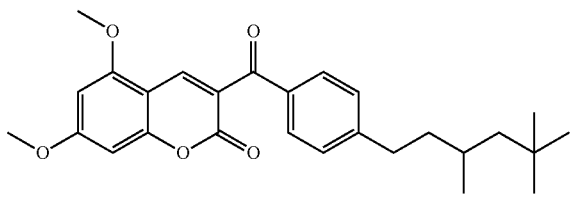 [SMILES: COc1cc(OC)c2cc(C(=O)c3ccc(CCC(C)CC(C)(C)C)cc3)c(=O)oc2c1]

Example 3.1

Preparation of methyl 3-oxo-3-(4-(3,5,5-trimethylhexyl)phenyl)propanoate

By operating as described in Example 1.1 and 1.2, but using as a starting product 3,5,5-trimethylhexylbenzene, the title compound is obtained. The title compound has been used directly in the following reaction without any further purification.

Example 3.2

Preparation of 5,7-dimethoxy-3-(4-(3,5,5-trimethylhexyl)benzoyl) coumarin

To a solution of 2 g (10.9 mmoles) 4,6-dimethoxy-2-hydroxy-benzaldehyde and 3.32 g (10.9 mmoles) methyl 3-oxo-3-(4-(3,5,5-trimethylhexyl)phenyl)propanoate in 50 ml ethanol, 0.5 ml piperidine is added. After 3 hours under reflux it has been cooled, and the reaction product is crystallized at ambient temperature. The product has been recovered by filtration as pale yellow solid and then crystallized twice from ethanol, thus obtaining 2.3 g title compound in the form of yellow powder (yield 48%).

$^1$H-NMR (CDCl3, δ ppm): 0.88 (s, 9H), 0.99 (d, 3H); 1.08-1.12 (m, 1H), 1.25-1.30 (m, 1H), 1.45-1.57 (m, 2H), 1.59-1.66 (m, 1H), 3.90 (s, 6H), 6.31 (d, 1H), 6.46 (d, 1H), 7.27 (d, 2H), 7.78 (d, 2H), 8.41 (s, 1H).

Example 4 (Comparative)

Preparation of 3-(4-hexylbenzoyl)-5,7-dimethoxycoumarin

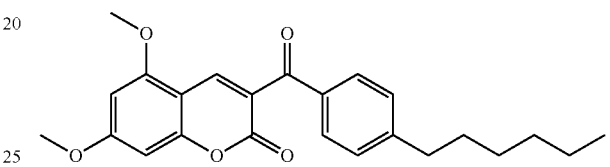

Example 4.1

Preparation of methyl-3-(4-hexylphenyl)-3-oxopropanoate

By operating as described in Examples 1.1 and 1.2, but using hexylbenzene as starting product, the title compound is obtained. The title compound has been used directly in the following reaction without any further purification.

Example 4.2

Preparation of 3-(4-hexylbenzoyl)-5,7-dimethoxycoumarin

To a solution of 2.78 g (15.25 mmoles) 4,6-dimethoxy-2-hydroxy-benzaldehyde and 4 g (15.25 mmoles) methyl-3-(4-hexylphenyl)-3-oxopropanoate in 40 ml ethanol, 0.5 ml piperidine has been added. After 3 hours under reflux the reaction mixture has been cooled and the reaction product has been crystallized at ambient temperature. 5 g title compound has been isolated as white solid (yield 83%).

$^1$H-NMR (CDCl3, δ ppm): 0.88 (t, 3H), 1.25-1.37 (m, 6H), 1.58-1.67 (m, 2H), 2.65-2.68 (t, 2H), 3.90 (d, 6H), 6.31 (d, 1H), 6.46 (d, 1H), 7.27 (d, 2H), 7.78 (d, 2H), 8.31 (s, 1H).

Example 5 (Comparative)

Preparation of 3-(4-dodecylbenzoyl)-5,7-dimethoxycoumarin

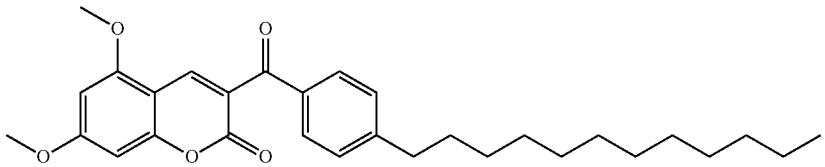 [SMILES: CCCCCCCCCCCCc1ccc(C(=O)c2cc3c(OC)cc(OC)cc3oc2=O)cc1]

Example 5.1

Preparation of methyl-3-(4-dodecylphenyl)-3-oxopropanoate

By operating as described in Examples 1.1 and 1.2, but using dodecylbenzene as starting product, the title compound is obtained. The title compound has been used directly in the following reaction without any further purification.

Example 5.2

Preparation of 3-(4-dodecylbenzoyl)-5,7-dimethoxycoumarin

To a solution of 1.58 g (8.66 mmoles) 4,6-dimethoxy-2-hydroxy-benzaldehyde and 3 g (8.66 mmoles) methyl-3-(4-dodecylphenyl)-3-oxopropanoate in 40 ml ethanol, 0.5 ml piperidine is added. After 3 hours under reflux it has been cooled, and the reaction product is crystallized at ambient temperature. The product has been recovered by filtration as pale yellow solid and then crystallized from ethanol, thus obtaining 2.5 g title compound in the form of white powder (yield 60%).

$^1$H-NMR (CDCl3, δ ppm): 0.88 (t, 3H), 1.22-1.38 (m, 18H), 1.60-1.68 (m, 2H), 2.65-2.68 (t, 2H), 3.90 (d, 6H), 6.31 (d, 1H), 6.46 (d, 1H), 7.27 (d, 2H), 7.78 (d, 2H), 8.41 (s, 1H).

Example 6

Comparative Tests

Example 6.1

Reactivity Assay

The performance in FT-IR (FT-IR 430-Jasco, with 400 nm LED lamp located at a distance of 65 mm and 30° angle from the sample) of blue inks for inkjet printing containing the photoinitiators with concentration of 5.0% by weight each, has been compared with the co-initiator Esacure EDB (IGM Resins B.V.) in a cyan ink for inkjet printing, in two different conditions:

A. The photopolymerizing solution has been prepared in the ink and stirred at about 40° C. for 1 hour, then the solution has been slowly brought back to ambient temperature and photopolymerized.

B. The photopolymerizing solution has been prepared in the ink and stirred at about 40° C. for 1 hour, then the solution has been slowly brought back to ambient temperature, filtered on a 0.45 microns Millipore® filter and, only at this point in time, photopolymerized.

The IR spectra have been acquired at constant time intervals during the photopolymerization, and the reduction over time of the peak area assigned to the acrylic double bonds at 1408 cm$^{-1}$ and 810 cm$^{-1}$ has been determined by using the IR software. This datum quantifies the degree of polymerization and thus the effectiveness of the photoinitiator.

The results at 400 nm, expressed as polymerization % over time, are depicted in the following Table 1:

TABLE 1

| Structure | Example | Test A after 0.5 sec | Test B after 0.5 sec |
|---|---|---|---|
| 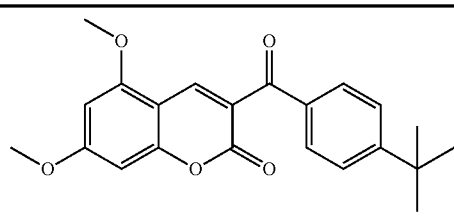 | Ex. 0 (comparative) | 67 | 61 |
| 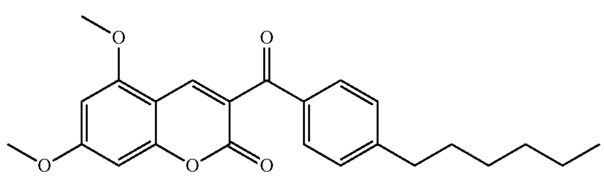 [SMILES: CCCCCCc1ccc(C(=O)c2cc3c(OC)cc(OC)cc3oc2=O)cc1] | Ex. 4 (comparative) | 75 | 67 |
| 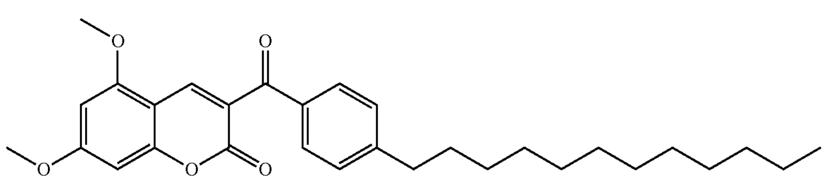 [SMILES: CCCCCCCCCCCCc1ccc(C(=O)c2cc3c(OC)cc(OC)cc3oc2=O)cc1] | Ex. 5 (comparative) | 42 | 37 |
| 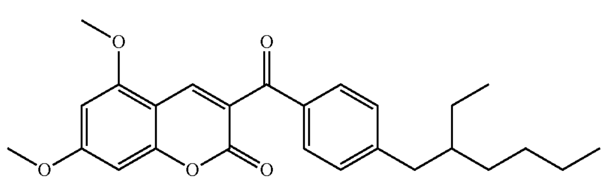 [SMILES: CCCCC(CC)Cc1ccc(C(=O)c2cc3c(OC)cc(OC)cc3oc2=O)cc1] | Ex. 1 | 75 | 75 |

TABLE 1-continued

| Structure | Example | Test A after 0.5 sec | Test B after 0.5 sec |
|---|---|---|---|
| 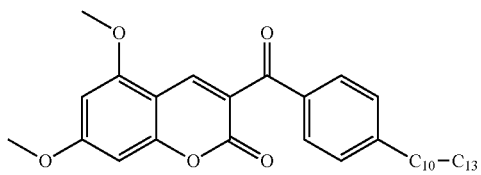 isomeric mixture | Ex. 2 | 74 | 74 |
| 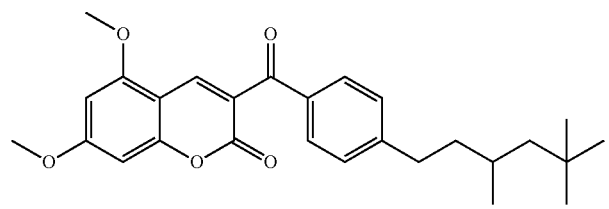 [SMILES: COc1cc(OC)c2cc(C(=O)c3ccc(CCC(C)CC(C)(C)C)cc3)c(=O)oc2c1] | Ex. 3 | 71 | 71 |

This test confirm that the compounds of Formula (I) show a clearly higher reactivity then the comparative compounds (Ex. 0, expressly described in Example 10 of WO2014/063997, Ex. 4 and Ex. 5).

Example 6.2

Yellowing Assay

The photopolymerizable compositions for the test have been prepared by dissolving the photoinitiators with a concentration of 3.0% by weight each and the co-initiators Esacure EDB (Test C) and Photomer 4250 (Test D) in a solution of PETIA (pentaerythritoltriacrylate) and Ebecryl 8602 (Allnex). Thus, the photopolymerizable composition has been laid with a thickness of 6 microns on a cardboard varnished by using a bar-coater. Subsequently, the laid composition has been photopolymerized by using a LED lamp at 395 nm (8 W/cm$^2$) and with a speed of 50 m/min. The film yellowing has been measured as b* value by using the BYK color guide 45/0. The results are shown in the following Table 2:

TABLE 2

| Structure | Example | Test C | Test D |
|---|---|---|---|
| 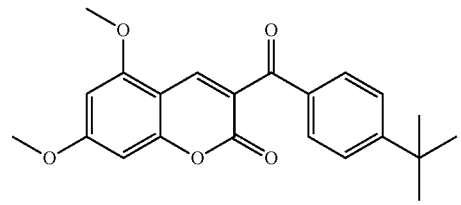 [SMILES: COc1cc(OC)c2cc(C(=O)c3ccc(C(C)(C)C)cc3)c(=O)oc2c1] | Ex. 0 (comparative) | 11.87 | 4.72 |
| 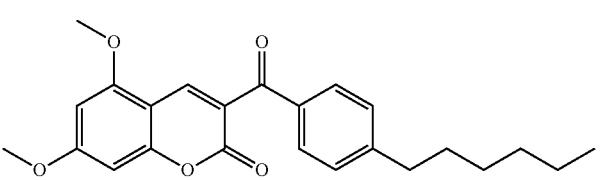 [SMILES: CCCCCCc1ccc(C(=O)c2cc3c(OC)cc(OC)cc3oc2=O)cc1] | Ex. 4 (comparative) | 9.87 | 4.04 |
| 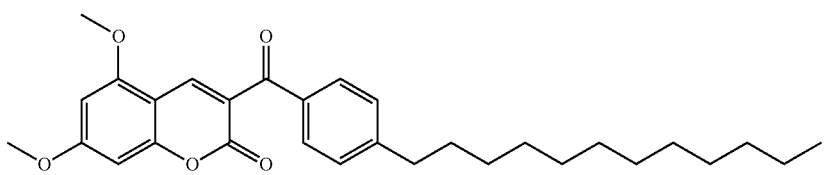 [SMILES: CCCCCCCCCCCCc1ccc(C(=O)c2cc3c(OC)cc(OC)cc3oc2=O)cc1] | Ex. 5 (comparative) | 8.13* | 3.30* |

TABLE 2-continued

| Structure | Example | Test C | Test D |
|---|---|---|---|
| 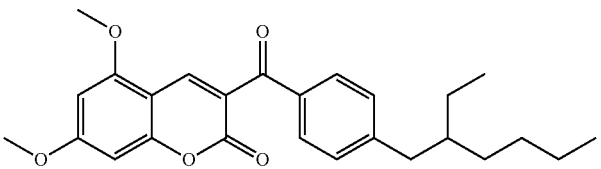 [SMILES: CCCCC(CC)Cc1ccc(C(=O)c2cc3c(OC)cc(OC)cc3oc2=O)cc1] | Ex. 1 | 8.90 | 4.47 |
| 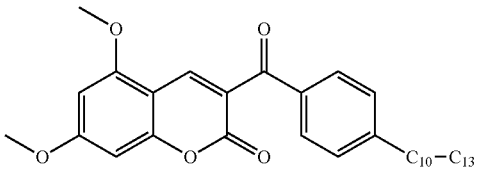 isomeric mixture | Ex. 2 | 9.36 | 3.48 |
| 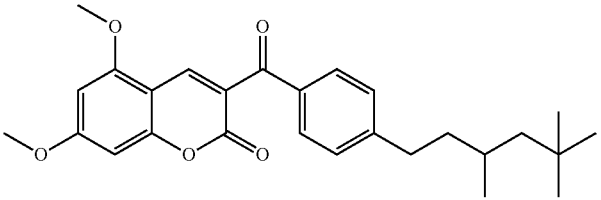 [SMILES: COc1cc(OC)c2cc(C(=O)c3ccc(CCC(C)CC(C)(C)C)cc3)c(=O)oc2c1] | Ex. 3 | 9.66 | 4.33 |

*Not completely dissolved.

It can be observed that the yellowing of the compounds of Formula (I) is lower than, or comparable with, the comparative compounds (Ex. 0, expressly described in Example 10 in WO2014/063997, Ex. 4 and Ex. 5).

Example 6.3

The same quantities by weight of a compound of Formula (I) and of a comparative compound (Ex. 0, expressly described in Example 10 of WO2014/063997) have been reacted.

Example 6.3.1

Transparent Formulation

The photopolymerizable compositions have been prepared by dissolving the photoinitiators at 3% by weight and the co-initiator Esacure EDB, in a 99.5/0.5 mixture by weight of Ebecryl 605 and Ebecryl 350 (Allnex).

Thus, a FT-IR reactivity test (FT-IR 430-Jasco, with 400 nm LED lamp located at a distance of 65 mm and 30° angle from the sample) has been carried out.

The IR spectra have been acquired at constant time intervals during the photopolymerization, and the reduction over time of the peak area assigned to the acrylic double bonds at 1408 cm$^{-1}$ and 810 cm$^{-1}$ has been determined by using the IR software. This datum quantifies the degree of polymerization and thus the effectiveness of the photoinitiator.

The results at 400 nm, expressed as polymerization % over time, are depicted in the following Table 3:

TABLE 3

| Structure | Example | % conversion of double bonds at 0.5 second illumination with 400 nm LED lamp |
|---|---|---|
| 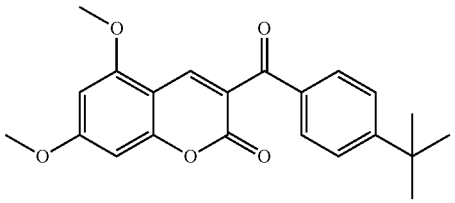 [SMILES: COc1cc(OC)c2cc(C(=O)c3ccc(C(C)(C)C)cc3)c(=O)oc2c1] | Ex. 0 | 80 |

TABLE 3-continued

| Structure | Example | % conversion of double bonds at 0.5 second illumination with 400 nm LED lamp |
|---|---|---|
| (5,7-dimethoxy coumarin with 3-(4-(C10H21–C13H27)benzoyl) substituent) isomeric mixture | Ex. 2 | 80 |

As mentioned, notwithstanding the moles of the tested compound of Formula (I) (Ex. 2) are about 30% less than those of the comparative compound, the conversion of double bonds is equivalent, demonstrating higher reactivity per mole of the compound of Ex. 2.

Example 6.3.2

Lithography Magenta Ink

The photopolymerizable compositions have been prepared by dissolving the photoinitiators and the co-initiator Esacure A198 with a concentration of 1.5% each, in a lithography magenta ink.

The ink is milled in a three roll mill until the granulometry lower than 1 micron is achieved and then is applied with a thickness of 1.5 microns through an IGT mechanical coater on a paper support; and then it is passed under a light source (Phoseon LED 395 nm, 16 W/cm$^2$). The photopolymerization speed is measured in linear speed (m/min), at which a complete photopolymerization (Through-cure) is taking place. The photopolymerization is complete when the ink doesn't show any damage after the repeated pressure and distortion of the thumb on the surface. The higher the linear speed for obtaining the Through-cure, the higher the reactivity of the photoinitiator.

The results of the test are in Table 4.

This example confirms the higher reactivity of the compound of Formula (I) of the invention described in Ex. 2 also when it is applied to a lithography ink.

The invention claimed is:

1. Compounds of Formula (I):

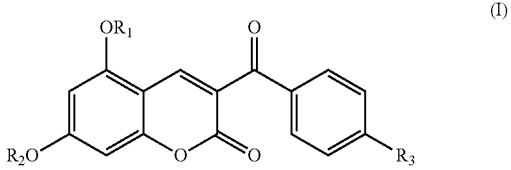

wherein:
  $R_1$ and $R_2$ are each a methyl group;
  $R_3$ is selected from a 2-ethylhexyl group, a mixture of $C_{10}$-$C_{13}$ alkyl linear and branched groups and a 3,5,5-trimethylhexyl group.

2. The compounds of Formula (I) according to claim 1, wherein $R_3$ is a mixture of $C_{10}$-$C_{13}$ alkyl linear and branched groups.

TABLE 4

| Structure | Example | Through-cure (m/min) |
|---|---|---|
| (5,7-dimethoxy coumarin with 3-(4-tert-butylbenzoyl) substituent) | Ex. 0 | 64 |
| (5,7-dimethoxy coumarin with 3-(4-(C10H21–C13H27)benzoyl) substituent) isomeric mixture | Ex. 2 | 77 |

3. The compounds of Formula (I) according to claim 2, wherein said mixture is constituted from 50 to 99% by alkyl $C_{10}$-$C_{13}$ linear groups and for the remaining percentage by their branched isomers.

4. The compounds of Formula (I) according to claim 3, wherein said mixture is constituted from 78 to 85% by alkyl $C_{10}$-$C_{13}$ linear groups and for the remaining percentage by their branched isomers.

* * * * *